United States Patent
Patzner et al.

(10) Patent No.: US 9,728,929 B2
(45) Date of Patent: Aug. 8, 2017

(54) METHOD FOR ELECTRICALLY CONNECTING A COAXIAL CONDUCTOR TO A CIRCUIT CARRIER

(71) Applicant: Robert Bosch GmbH, Stuttgart (DE)

(72) Inventors: Patrik Patzner, Leonberg-Silberberg (DE); Markus Reinhard, Kornwestheim (DE); Alexander Lux, Ostfildern (DE)

(73) Assignee: Robert Bosch GmbH, Stuttgart (DE)

( * ) Notice: Subject to any disclaimer, the term of this patent is extended or adjusted under 35 U.S.C. 154(b) by 160 days.

(21) Appl. No.: 14/762,560

(22) PCT Filed: Jan. 7, 2014

(86) PCT No.: PCT/EP2014/050116
§ 371 (c)(1),
(2) Date: Jul. 22, 2015

(87) PCT Pub. No.: WO2014/114479
PCT Pub. Date: Jul. 31, 2014

(65) Prior Publication Data
US 2015/0364892 A1 Dec. 17, 2015

(30) Foreign Application Priority Data
Jan. 22, 2013 (DE) .................... 10 2013 200 971

(51) Int. Cl.
*H01R 24/50* (2011.01)
*H01R 43/20* (2006.01)
(Continued)

(52) U.S. Cl.
CPC ........... *H01R 43/205* (2013.01); *G01N 33/22* (2013.01); *H01R 9/0515* (2013.01); *Y10T 29/49176* (2015.01)

(58) Field of Classification Search
CPC .. H01R 2103/00; H01R 24/50; H01R 9/0515; H01R 13/5216
(Continued)

(56) References Cited

U.S. PATENT DOCUMENTS 3,742,425 A    6/1973  Peltola et al.
3,879,103 A *  4/1975  Peltola ................. H01R 9/0515
                                                          439/581
(Continued)

FOREIGN PATENT DOCUMENTS

DE              34 12 704         10/1984
DE         20 2011 104969         10/2011
(Continued)

*Primary Examiner* — Gary Paumen
(74) *Attorney, Agent, or Firm* — Norton Rose Fulbright US LLP; Gerard Messina

(57) ABSTRACT

A method is described for electrically connecting a coaxial conductor to a circuit carrier, in particular a printed circuit board. The circuit carrier has a top side and a bottom side, and printed conductors are situated at least on the top side of the circuit carrier. The coaxial conductor also includes an inner conductor and an outer conductor, the coaxial conductor being led, at least partially, from the bottom side of the circuit carrier through a feedthrough provided in the circuit carrier. In addition, at least one first contact conductor is used for electrically connecting the outer conductor to at least one first printed conductor of the circuit carrier, and at least one second contact conductor is used for electrically connecting the inner conductor to at least one second printed conductor of the circuit carrier. The first and the second contact conductors each have a press-in connection at at least one of their contact points with the circuit carrier or with the coaxial conductor.

13 Claims, 2 Drawing Sheets

(51) Int. Cl.
  *H01R 9/05* (2006.01)
  *G01N 33/22* (2006.01)
(58) Field of Classification Search
  USPC .................................. 439/581, 63, 329, 936
  See application file for complete search history.

(56) References Cited

U.S. PATENT DOCUMENTS

| | | | | |
|---|---|---|---|---|
| 3,910,665 | A * | 10/1975 | Stull ...................... | H01R 24/50 |
| | | | | 439/581 |
| 4,230,385 | A * | 10/1980 | Ammon ................ | H01R 12/585 |
| | | | | 174/262 |
| 4,396,242 | A * | 8/1983 | Kurano ................. | H01R 24/50 |
| | | | | 439/581 |
| 4,651,085 | A * | 3/1987 | Sakurai .............. | G01N 33/2852 |
| | | | | 324/636 |
| 5,797,765 | A * | 8/1998 | Barnett ................. | H01R 24/50 |
| | | | | 333/260 |
| 6,939,175 | B2 * | 9/2005 | Parrish ............... | G01R 1/07378 |
| | | | | 439/620.03 |
| 7,364,461 | B1 * | 4/2008 | Back ................... | H01R 9/0515 |
| | | | | 439/329 |
| 2001/0051448 | A1 * | 12/2001 | Gonzales ............... | H01R 24/50 |
| | | | | 439/63 |
| 2005/0208828 | A1 * | 9/2005 | Miller .................. | H01R 9/0515 |
| | | | | 439/581 |

FOREIGN PATENT DOCUMENTS

| | | |
|---|---|---|
| EP | 0 971 441 | 1/2000 |
| JP | H05-54919 A | 3/1993 |

\* cited by examiner

METHOD FOR ELECTRICALLY CONNECTING A COAXIAL CONDUCTOR TO A CIRCUIT CARRIER

FIELD OF THE INVENTION

The present invention is directed to methods and devices for determining the composition of fuel mixtures.

BACKGROUND INFORMATION

The fuel mixtures which, in addition to the actual petroleum fuels, may contain a blend of ethanol and/or other alcohols are being increasingly used in motor vehicles. For example, so-called flex-fuel vehicles are known which may be operated with variable ethanol/gasoline mixtures. The parameters of the engine control of the motor vehicle are typically adapted to the composition of the fuel mixture. The ethanol-fuel mixture ratio is either generally determined based on measuring variables that are present, with the aid of software in the control unit itself, or this mixture ratio may be recognized using an ethanol sensor. Ethanol sensors of this type may be based on many different measuring principles. In particular, capacitance measuring methods based on the permittivity and the conductivity determination are used here. The permittivity of the fuel mixture is generally determined at frequencies of up to approximately 1 MHz.

To identify further components such as water, measurements in the GHz range are necessary, since in this range the permittivity of alcohol, water, and other polar components, for example interfering components, decreases greatly with increasing frequency due to the orientation polarization. One known measuring method is the measurement of an absorption, transmission, or reflection of microwaves by the fuel mixture. An example of such a method which operates in the GHz range is discussed in DE 34 12 704 A1.

In addition, a method is discussed in DE 10 2008 044 403 A1 for determining a composition of a fuel mixture, in which a characteristic pattern of a certain response to microwave irradiation is detected over a fairly great frequency range in order to ascertain the properties of the fuel mixture, and the composition of the fuel mixture is deduced therefrom. One particular advantage of the method discussed in DE 10 2008 044 403 A1 is that the accuracy may be increased by using greater frequency ranges, so that alcohol-fuel mixtures, for example, which additionally contain a water component and/or additives may be characterized much more accurately than with conventional methods.

In measuring methods in the microwave range or high-frequency range, connectors and cables having a coaxial design are usually used for attaching a microwave conductor. In particular, in these types of fuel sensors a sensor electronics system which is provided for at least partial evaluation or signal processing may be situated in the immediate vicinity of the measuring element, and is connected to the coaxial connector of the measuring element in order to couple the detected microwave signal. Due to the high demands on the signal quality and the signal transmission, it is known to use bond connections or solder connections, which at the same time provide necessary thermal decoupling.

However, there is potential for improvement with regard to the coupling of the microwave signal into the sensor electronics system.

SUMMARY OF THE INVENTION

Accordingly, a method and a device are provided which are usable for electrically connecting a coaxial conductor to a circuit carrier, in particular a printed circuit board. The method according to the present invention initially provides that the circuit carrier has a top side and a bottom side, printed conductors may be situated at least on the top side of the circuit carrier for implementing and providing a sensor electronics system. The coaxial conductor also includes an inner conductor and an outer conductor which, as is known, may be separated by an electrically insulating dielectric, for example an epoxy resin, and which encloses the inner conductor and the dielectric. In addition, it is provided according to the present invention that the coaxial conductor is led, at least partially, from the bottom side of the circuit carrier through a feedthrough provided in the circuit carrier. The feedthrough may be formed, for example, by a corresponding borehole through the circuit carrier, the feedthrough may have an inner diameter which is larger than the outer diameter of the coaxial conductor. Furthermore, it is provided according to the present invention that at least one first contact conductor is used for electrically connecting the outer conductor to at least one first printed conductor of the circuit carrier, and that at least one second contact conductor is used for electrically connecting the inner conductor to at least one second printed conductor of the circuit carrier.

A contact conductor is generally understood to mean an electrical conductor which may be made of metal and which may have a predetermined profiled shape. The contact conductor is used essentially for providing an electrically conductive connection between at least the first printed conductor and the outer conductor, and between at least one second printed conductor and the inner conductor of the coaxial conductor. For this purpose, it is further provided that the first and the second contact conductors each have a press-in connection at least one of their contact points with the circuit carrier or with the coaxial conductor. The press-in connection according to the present invention may be established by press-in contacts. According to the present invention, this advantageously provides an option for easily providing a connection which meets the requirements for signal quality in the signal transmission, and also stability and reliability of the connecting point, with little mechanical effort.

Using a press-in connection also provides the advantage that due to the fact that the connection is thus a solder-free electrical connection, the formation or development of undesirable solder bridges during production as well as the age-related occurrence of so-called cold solder joints during subsequent use of the circuit carrier and the coaxial conductor are advantageously avoided. For this purpose, the contact conductors may be made of copper or a copper alloy, such as so-called beryllium copper. Other alloys having comparable properties are likewise conceivable.

During pressing in according to the present invention of the contact conductors, in particular into boreholes provided in the circuit carrier for this purpose, which are lined, for example, with a metallic and in particular electrically conductive sleeve, a slight deformation of the pressed-in contact conductor into the borehole establishes a gas-tight electrical connection which is characterized in a particularly advantageous manner by high reliability and longevity.

In addition, the contact conductors may be geometrically configured in such a way that they have freedom of movement necessary for thermal decoupling. Due to the differing materials of the circuit carrier and of the coaxial conductor, a change in the temperature likewise results in different expansions of the circuit carrier and of the coaxial conductor. The contact conductor may also be configured to compensate for the differing expansion coefficients due to the different material properties of the circuit carrier and the coaxial conductor. In particular, for compensating for the differing thermal expansion coefficients of the circuit carrier and the coaxial conductor it is advantageous that damage, in particular in the area of the contact points between the contact conductor and the coaxial conductor and the circuit carrier in each case, due to temperature changes, and thus an increase in the contact resistances over the service life, is advantageously avoided due to the geometry of the contact conductors.

Furthermore, it may be provided in the method according to the present invention that the first and/or the second contact conductor include(s) a ring-shaped conductor section. In particular also with regard to the above-described advantage, this contributes to the compensation for differing temperature/thermal expansion coefficients, in that rigidity in the contact conductor itself is provided which withstands lateral shear forces or tensile forces that may possibly occur.

According to another exemplary embodiment of the method, it may also be provided that the first contact conductor contacts the outer conductor approximately over the entire circumference. It may be advantageous here, for example, when the first contact conductor includes a ring-shaped conductor section to be able to compensate, over the circumference, for currents or potentials which may possibly be transmitted to the outer conductor, which is used in particular for shielding, and to optionally allow the currents or potentials to be introduced, which may be over a large surface area and with a low contact resistance, via a plurality of contact points with a first printed conductor of the circuit carrier, which may be connected to a ground conductor for potential equalization. In addition, an optionally provided ring-shaped conductor section in the first contact conductor provides the advantage of contacting over a large surface area, which may also be achieved by a plurality of contact strips. Furthermore, the number of contact points of the first contact conductor with the circuit carrier, in particular with a first printed conductor of the circuit carrier, may differ from the number of contact strips which contact the outer conductor or the inner conductor.

The second contact conductor may likewise include a ring-shaped conductor section for increasing the rigidity and dimensional stability.

In addition, according to another specific embodiment of the method, it may be advantageous when the first and/or the second contact conductor in the area of contact with the outer conductor or the inner conductor, respectively, have/has a C-shaped section, and act(s) on the outer conductor and/or the inner conductor with an elastic force for the contacting. The concept underlying the present invention, of connecting the contact conductor with the aid of a press-in connection, is ensured and refined on the side facing the coaxial conductor in such a way that the contacting sections which are bent in the shape of a C have a smaller opening diameter than the outer diameter of the outer conductor. According to this exemplary embodiment, when the first contact conductor is attached to the outer conductor of the coaxial conductor, the plurality of contact strips bent in the shape of a C is displaced outwardly by the difference in the two above-mentioned diameters, and thus continues to exert an elastic force on the outer conductor. The same similarly applies for optionally provided contacting sections of the second contact conductor which are bent in the shape of a C, and which likewise circumferentially contact an inner conductor which may be axially extended with respect to the outer conductor via an exposure on same.

Alternatively or additionally, it may also be provided that for the electrical connection, the first and/or the second contact conductor is/are soldered and/or welded to the first printed conductor and/or the second printed conductor on correspondingly provided contacting surfaces. Laser soldering, or alternatively, reflow soldering or iron soldering, may be used as the soldering process. Laser welding in particular has proven advantageous as the welding process, although gap welding or step welding may also be used.

In the case of a press-in connection at the contact points of the first and the second contact conductors to the first and second printed conductor, respectively, on the circuit carrier, it may also be provided in the provided method that the first and/or the second contact conductor is/are connected to the outer conductor or the inner conductor, respectively, by a solder joint or weld joint. Use of the above-mentioned soldering processes and welding processes is likewise conceivable for this purpose.

According to a further embodiment of the method provided according to the present invention, it may also be provided that the first contact conductor is situated on the bottom side of the circuit carrier. Contacting of the first contact conductor with the outer conductor is easily possible, and corresponding contacting of the contact conductor with the first printed conductor of the circuit carrier is ensured due to the lining of the boreholes in the circuit carrier with electrically conductive eyes which customarily provide a via of the circuit carrier from the top side to the bottom side. Inadvertent development of a short circuit between the first contact conductor and the second contact conductor is thus likewise advantageously avoided.

Alternatively or additionally, it may be provided that the first printed conductor and the second printed conductor are situated on opposite sides of the circuit carrier. The first printed conductor of the circuit carrier, which is to be connected to the first contact conductor, may be situated on the same side as described above, for example on the bottom side of the circuit carrier. This is particularly advantageous when the outer conductor of the coaxial conductor, via the first contact conductor, may be to be connected to ground via the first printed conductor for potential equalization. For further shielding, it is likewise conceivable for the first printed conductor to be formed, on the bottom side of the circuit carrier, in the form of a copper coating over a large surface area.

In addition, it may likewise be provided in the method provided according to the present invention that the first and/or the second contact conductor has/have a plastic extrusion coating. Due to the plastic extrusion coating, in the case of the first and the second contact conductors being situated on the top side of the circuit carrier, inadvertent contact formation between the first contact conductor and the second contact conductor may likewise be avoided.

The following method steps, for example, may be provided in the provided method. It may be initially provided, for example, that the coaxial conductor is joined into the feedthrough of the circuit carrier, and the first or the second contact conductor is subsequently contacted with the outer conductor or the inner conductor, respectively, and the circuit carrier by pressing in the first or the second contact conductor from the top side of the circuit carrier, for example into the provided borehole. It may also be subsequently be provided that the respective other contact conductor is contacted with the outer conductor or the inner conductor, respectively, and the circuit carrier, which may be in the same way.

Furthermore, a sensor device according to the present invention for detecting at least one property of a medium, in particular for detecting a composition of a fuel mixture, is provided, which according to the present invention includes at least one sensor and at least one circuit carrier which is electrically connected to the sensor. The circuit carrier may have a top side and a bottom side, printed conductors being situated at least on the top side of the circuit carrier. According to the present invention, the sensor also includes a coaxial conductor which includes an inner conductor and an outer conductor. In particular, it is also provided that the coaxial conductor is led, at least partially, from the bottom side of the circuit carrier through a feedthrough provided in the circuit carrier. It is also provided that the outer conductor is connected to at least one first printed conductor of the circuit carrier with the aid of at least one first contact conductor, and that the inner conductor is connected to at least one second printed conductor of the circuit carrier with the aid of at least one second contact conductor. In addition, it may be provided that the first and the second contact conductors each have a press-in connection at least one of their contact points with the circuit carrier or with the coaxial conductor. The device provided according to the present invention in particular has the same advantages as the above-described method according to the present invention.

Exemplary embodiments of the present invention are illustrated in the figures and explained in greater detail in the following description.

DETAILED DESCRIPTION

Figure 1A:
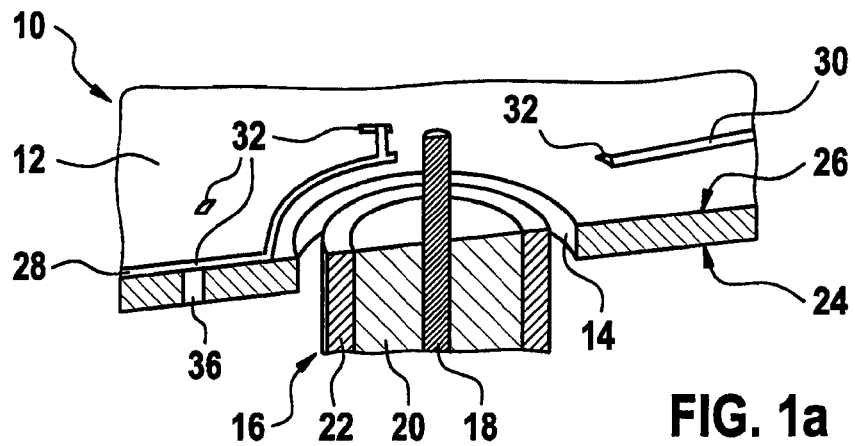
FIG. 1a shows a schematic sectional illustration of a portion of the specific embodiment of the sensor device after a first method step, in particular after joining the circuit carrier to the coaxial conductor.
Figure 1B:
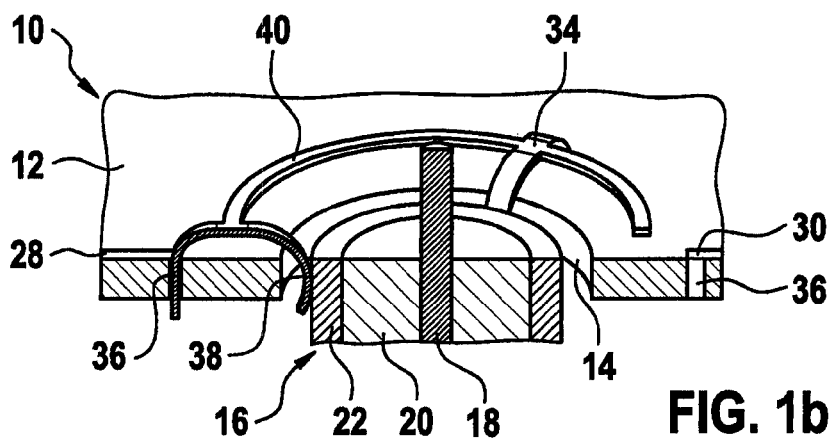
FIG. 1b shows a schematic sectional illustration of a portion of the specific embodiment of the sensor device after a further method step, in particular after contacting the first contact conductor with the outer conductor and the circuit carrier.
Figure 1C:
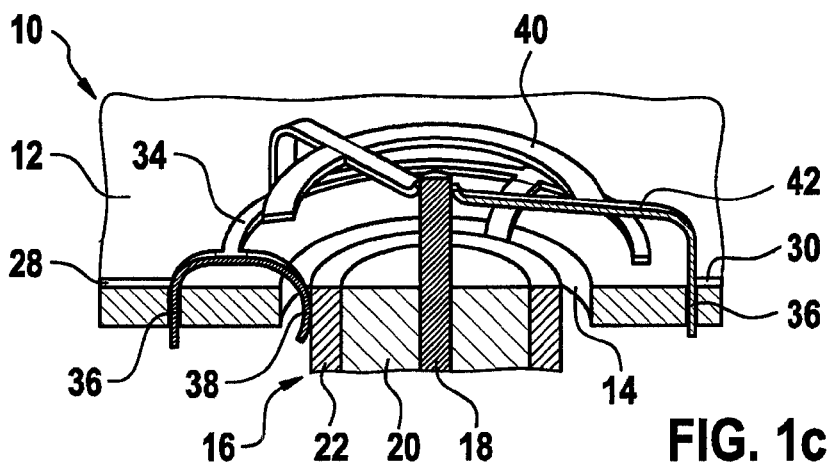
FIG. 1c shows a schematic sectional illustration of a specific embodiment of the sensor device according to the present invention after yet a further method step, in particular after contacting the second contact conductor with the inner conductor and the circuit carrier.

FIGS. 1a through 1c show schematic sectional illustrations of one specific embodiment of sensor device 10 in various stages of the embodiment of the method according to the present invention.

FIG. 1a shows a circuit carrier 12 which includes a feedthrough 14 into which a coaxial conductor 16 is joined. Coaxial conductor 16 includes, in a known manner, an inner conductor 18, and an outer conductor 22 which is separated from inner conductor 18 by a dielectric 20. As is apparent from the illustration, inner conductor 18 of coaxial conductor 16 has an end section which protrudes from dielectric 20 on the end face side.

According to a first method step, for mounting coaxial conductor 16 and circuit carrier 12, coaxial conductor 16 is joined in such a way that coaxial conductor 16 may protrude into, and/or protrudes in sections through feedthrough 14, from a bottom side 24 of circuit carrier 12. Circuit carrier 12 has a top side 26, opposite from its bottom side 24, on which a first printed conductor 28 and a second printed conductor 30 are situated. Furthermore, it is apparent from a detail in FIG. 1a that circuit carrier 12 includes contact points 32 which are partially in an electrically conductive connection with either first printed conductor 28 or second printed conductor 30. In addition, contact points 32 may likewise be provided which are not connected to either first printed conductor 28 or to second printed conductor 30.

Furthermore, the illustration in FIG. 1b depicts the previously shown specific embodiment of sensor device 10 after a further method step, according to which a first contact conductor 34 has been contacted with contact points 32 of circuit carrier 12, which are provided for this purpose and connected to first printed conductor 28, and has also been contacted with outer conductor 22 of coaxial conductor 16. For this purpose, first contact conductor 34 may be inserted here from top side 26 of circuit carrier 12 into corresponding contact points 32 provided for this purpose, which may be establishing a press-in connection. For this purpose, contact points 32 may be configured as a via 36 in the form of an electrically conductive contact sleeve. At the same time, first contact conductor 34 with a C-shaped section 38 of first contact conductor 34 surrounds outer conductor 22 of coaxial conductor 16. For this purpose, first contact conductor 34 may be configured in such a way that formed C-shaped sections 38 form an opening which may have a slightly smaller diameter than the outer diameter of coaxial conductor 16, in particular of outer conductor 22. As a result, C-shaped sections 38 of first contact conductor 34 are slightly expanded by outer conductor 22 when they are attached to same, and subsequently exert an elastic force for secure contacting with outer conductor 22. In addition, it is apparent from a detail in FIG. 1b that first contact conductor 34 includes a ring-shaped conductor section 40 which imparts greater rigidity and stability to first contact conductor 34.

The illustration in FIG. 1c shows the configuration of sensor device 10 according to the present invention after a further method step, according to which a second contact conductor 42 for contacting inner conductor 18 of coaxial conductor 16 to second printed conductor 30 is introduced into contact point 32 correspondingly provided for this purpose. The introduction of second contact conductor 42 into contact points 32 of circuit carrier 12 provided for this purpose may likewise take place with establishment of a press-in connection. According to the illustration in FIG. 1c, the second contact conductor likewise includes a ring-shaped conductor section 40, and may have a profile that is shaped in such a way that inadvertent contacting of first contact conductor 34 with second contact conductor 42 is prevented. For this purpose, for example a plastic extrusion coating, not illustrated, of first contact conductor 34 and/or of second contact conductor 42 may also be provided which prevents the inadvertent creation of a short circuit between first contact conductor 34 and second contact conductor 42.

According to the illustrated specific embodiment, second contact conductor 42 likewise has a press-in connection for contacting inner conductor 18 of coaxial conductor 16.

Figure 2:
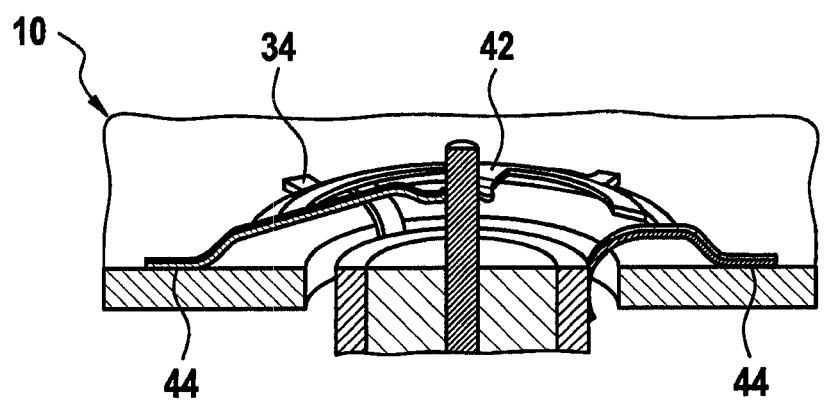
FIG. 2 shows a schematic sectional illustration of another specific embodiment of the sensor device according to the present invention.

The illustration in FIG. 2 shows another specific embodiment of sensor device 10 according to the present invention, according to which it may be further provided that first contact conductor 34 and second contact conductor 42 are held, for example, only at each second contact point 32 of circuit carrier 12 to form a press-in connection, and are fastened at the respective other contact points 32 via a correspondingly provided contacting surface 44 with formation of a solder joint or a weld joint.

Figure 3:
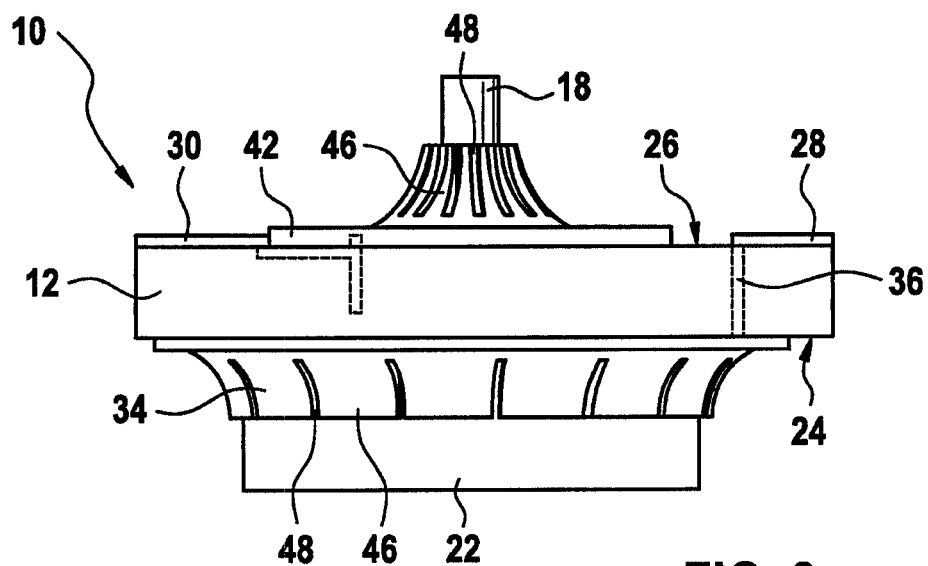
FIG. 3 shows a schematic side view of another possible specific embodiment of the sensor device according to the present invention.

According to another specific embodiment of sensor device 10 according to the present invention, it may be provided, as illustrated in FIG. 3, that first contact conductor 34 is situated on bottom side 24 of circuit carrier 12, and is connected to first printed conductor 28 on top side 26 of circuit carrier 12, for example with the aid of a via 36. However, it is also conceivable that first printed conductor 28 may likewise be situated on bottom side 24 of circuit carrier 12.

In addition, it is apparent from the illustration in FIG. 3 that first contact conductor 34 and also second contact conductor 42 each have a plurality of contact strips 46 which may be formed, for example, by introducing slits 48, and which after being attached to inner conductor 18 or outer conductor 22 of coaxial conductor 16 acts on same with an elastic force, similarly as for C-shaped sections 38 of the specific embodiment described above.

What is claimed is:

1. A method for electrically connecting a coaxial conductor to a circuit carrier, the method comprising:
   electrically connecting, via at least one first contact conductor, an outer conductor to at least one first printed conductor of the circuit carrier, wherein the circuit carrier has a top side and a bottom side, the at least one printed conductor being situated at least on the top side of the circuit carrier, the coaxial conductor including an inner conductor and the outer conductor, the coaxial conductor being led, at least partially, from the bottom side of the circuit carrier through a feedthrough provided in the circuit carrier; and
   electrically connecting, via at least one second contact conductor, the inner conductor to at least one second printed conductor of the circuit carrier;
   wherein the first and the second contact conductors each have a press-in connection at at least one of their contact points with the circuit carrier or with the coaxial conductor;
   wherein at least one of the first contact conductor and the second contact conductor in the area of contact with the outer conductor or the inner conductor, respectively, has a C-shaped section, and acts on at least one of the outer conductor and the inner conductor with an elastic force for the contacting.

2. The method of claim 1, wherein the at least one of the first contact conductor and the second contact conductor includes a ring-shaped conductor section.

3. The method of claim 1, wherein the first contact conductor contacts the outer conductor approximately over the entire circumference.

4. The method of claim 1, wherein the first and the second contact conductor in the area of contact with the outer conductor or the inner conductor, respectively, has a C-shaped section, and acts on the outer conductor and the inner conductor with an elastic force for the contacting.

5. The method of claim 1, wherein for the electrical connection, the at least one of the first contact conductor and second contact conductor is at least one of soldered and welded to the first printed conductor and/or the second printed conductor on correspondingly provided contacting surfaces.

6. The method of claim 1, wherein the at least one of the first contact conductor and the second contact conductor is connected to the outer conductor or the inner conductor, respectively, by a solder joint or weld joint.

7. The method of claim 1, wherein the first contact conductor is situated on the bottom side of the circuit carrier.

8. The method of claim 1, wherein the first printed conductor and the second printed conductor are situated on opposite sides of the circuit carrier.

9. The method of claim 1, wherein at least one of the first contact conductor and the second contact conductor includes a plastic extrusion coating.

10. The method of claim 1, further comprising:
    joining the coaxial conductor into the feedthrough;
    contacting the first or second contact conductor with the outer conductor or the inner conductor, respectively, and the circuit carrier;
    contacting the respective other contact conductor with the outer conductor or the inner conductor, respectively, and the circuit carrier.

11. The method of claim 1, wherein the circuit carrier includes a printed circuit board.

12. A sensor device for detecting at least one property of a medium, comprising:
    at least one sensor; and
    at least one circuit carrier which is electrically connected to the sensor;
    wherein the circuit carrier has a top side and a bottom side, printed conductors being situated at least on the top side of the circuit carrier, the sensor also including at least one coaxial conductor which includes an inner conductor and an outer conductor, the coaxial conductor being fed, at least partially, from the bottom side of the circuit carrier through a feedthrough provided in the circuit carrier, wherein the outer conductor is connected to at least one first printed conductor of the circuit carrier with at least one first contact conductor, and the inner conductor is connected to at least one second printed conductor of the circuit carrier with at least one second contact conductor, the first and the second contact conductors each having a press-in connection at at least one of their contact points with the circuit carrier or with the coaxial conductor;
    wherein at least one of the first contact conductor and the second contact conductor in the area of contact with the outer conductor or the inner conductor, respectively, has a C-shaped section, and acts on at least one of the outer conductor and the inner conductor with an elastic force for the contacting.

13. The sensor device of claim 12, wherein the medium includes a composition of a fuel mixture.

* * * * *